(12) United States Patent
Gustafsson

(10) Patent No.: US 6,210,424 B1
(45) Date of Patent: Apr. 3, 2001

(54) SURGICAL DEVICE

(75) Inventor: Sven Gustafsson, Värmdö (SE)

(73) Assignee: Dicamed AB, Sollentuna (SE)

( * ) Notice: Subject to any disclaimer, the term of this patent is extended or adjusted under 35 U.S.C. 154(b) by 0 days.

(21) Appl. No.: 09/380,244

(22) PCT Filed: Mar. 5, 1998

(86) PCT No.: PCT/SE98/00397

§ 371 Date: Aug. 30, 1999

§ 102(e) Date: Aug. 30, 1999

(87) PCT Pub. No.: WO98/43546

PCT Pub. Date: Oct. 8, 1998

(30) Foreign Application Priority Data

Mar. 18, 1997 (SE) .................................................. 9700990

(51) Int. Cl.⁷ .................................................. A61B 17/28
(52) U.S. Cl. .................................................. 606/206
(58) Field of Search .................................. 606/205, 206, 606/207

(56) References Cited

U.S. PATENT DOCUMENTS

| 4,367,746 | 1/1983 | Derechinsky . |
| 4,452,106 | 6/1984 | Tartaglia . |
| 4,601,283 | 7/1986 | Chikama . |
| 4,635,634 | 1/1987 | Santos . |
| 4,681,107 | 7/1987 | Kees, Jr. . |
| 5,242,458 | * 9/1993 | Bendel et al. .................. 606/205 |
| 5,254,130 | 10/1993 | Poncet et al. . |
| 5,304,203 | * 4/1994 | El Mallawany et al. ......... 606/207 |
| 5,403,342 | * 4/1995 | Tovey et al. .................... 606/205 |

FOREIGN PATENT DOCUMENTS

| 0567146A3 | 10/1993 | (EP) . |
| 0631759A1 | 1/1995 | (EP) . |

* cited by examiner

*Primary Examiner*—Michael Buiz
*Assistant Examiner*—Vy Qi Bui
(74) *Attorney, Agent, or Firm*—Burns, Doane, Swecker & Mathis, L.L.P.

(57) ABSTRACT

The present invention relates to a surgical device (1) comprising: an elongate, flexible and tubular arm (3) having a distal end and a proximal end; a flexible pulling means (6) which is arranged inside the arm (3); a tool (4) which is arranged at the distal end of the arm (3) and which comprises at least two parts (11,12), which are operable by said pulling means (6); and an operating means (15) which is arranged at the proximal end of the arm to operate said pulling means (6) and, thus, said tool (4). The invention is characterised in that said arm (3) is made of a material, which resumes its shape by heating and which has a transformation temperature which allows the arm (3) to be deformable to the desired shape at room temperature and to keep the thus obtained shape at a patient's body temperature during use of the device (1), so as then to allow resumption of its original shape when exposed to a temperature exceeding the body temperature.

20 Claims, 1 Drawing Sheet

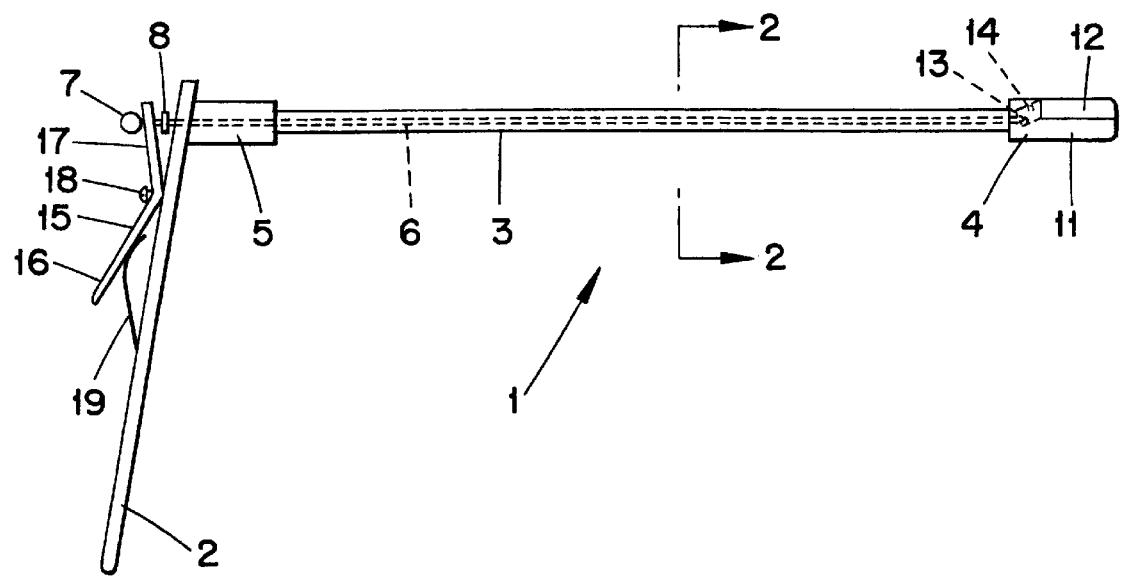

SURGICAL DEVICE

This invention relates generally to a surgical device. The invention concerns specifically a surgical device comprising:
- an elongate, flexible and tubular arm having a distal end and a proximal end;
- a flexible pulling means which is movably arranged inside the arm essentially over the entire length thereof;
- a tool which is arranged at the distal end of the arm and comprises at least two parts, which are arranged movable in relation to each other by operation of said pulling means; and
- an operating means which is arranged at the proximal end of the arm to operate said pulling means and, thus, said tool.

FIELD OF THE INVENTION AND BACKGROUND ART

In surgical operations, use is frequently made of special surgical devices which can be adjusted to allow access to target areas or spaces which are otherwise difficult to reach. For instance, in so-called endoscopy, use is often made of devices comprising a tubular, elongate arm which is provided with a tool arranged at its one end, the tool being operable by means of a pull rod which extends inside the arm essentially over the entire length thereof. Moreover, the arm can be bent to be adjusted to the particular application.

A problem is the fact that these devices obtain remaining deformations owing to bendings. Consequently, the more the device is used, the more remaining deformations. Thus, it will be more and more difficult to give the device the desired shape.

A further problem is the fact that the pull rod in the tubular arm slides more and more sluggishly, the more deformations the device obtains.

There is thus a need for an improved surgical device of the type described by way of introduction, which obviates the above-mentioned problems associated with prior art technique.

An object of the present invention therefore is to provide a surgical device, which can easily be given its original shape.

SUMMARY OF THE INVENTION

The above-mentioned object is achieved by a surgical device which is essentially characterised in that said arm is made of a material which resumes its shape by heating, preferably a memory metal, which has a transformation temperature that allows the arm to be deformable to the desired shape at room temperature and to keep the thus obtained shape at a patient's body temperature during use of the device, so as then to allow resumption of its original shape when it is exposed to a temperature exceeding the body temperature.

Further developments of the surgical device are evident from the distinguishing features stated in the sub-claims.

Several advantages are achieved by the invention, for instance, the device is ready for use after sterilisation by autoclave treatment, in which it resumes its original shape.

Further advantages and distinguishing features will appear from the following specification.

BRIEF DESCRIPTION OF THE DRAWINGS

The present invention will now be described in more detail by way of embodiments and with reference to the accompanying drawing, in which:

FIG. 1 is a schematic view of the device according to an embodiment of the invention; and FIG. 2 is a sectional view of the device along line 2—2 in FIG. 1.

DETAILED DESCRIPTION OF PREFERRED EMBODIMENTS

With reference to FIGS. 1 and 2, a surgical device 1 according to a currently preferred embodiment of the present invention is shown. The device 1 comprises a handle 2, an elongate, flexible and tubular arm 3, which is essentially circular in cross-section, and a tool 4. The arm 3 has a distal end, which is rotatably fixed to the handle 2 by means of a fixing device 5, and a proximal end, at which the tool 4 is mounted. Moreover a flexible pull rod 6 is arranged inside the arm 3 and extends beyond the proximal end of the arm 3, where it is provided with a first and a second stop element 7, 8, respectively, which are arranged at a distance from each other and formed as extensions of the pull rod 6.

At the handle 2, a V-shaped operating device 15 is arranged and intended to operate the pull rod 6 and, consequently, the tool 4. To this end, the operating device 15 comprises a first lever 16 which is connected to a second lever 17 and is angled in relation thereto. The operating device 15 is tiltably fixed to the handle 2 by means of a fixing element 18 in such a manner that when the first lever 16 is pressed towards the handle 2, the second lever 17 is made to tilt away from the handle 2 and vice versa. A pressure spring 16 is arranged between the handle 2 and the first lever 16 in a biasing fashion, the first lever 16 in the normal position being pressed away from the handle 2 and, consequently, the second lever 17 is pressed towards the handle. Moreover, the second lever 17 engages the pull rod 6 between the stop elements 7 and 8, the second lever 17 in the normal position pressing against the second stop element 8 to hold the pull rod 6 in an extended position. When a force of pressure is applied to the first lever 16 to press this towards the handle 2 against the action of the spring force, the operating device 15 tilts in relation to the fixing element 18, such that the second lever 17 is moved away from the handle 2. Thus, the second lever 17 presses the first stop element 7, whereby the pull rod 6 is moved to a retracted position.

The tool 4, which is arranged at the distal end of the arm, comprises a stationary jaw 11 and a movable jaw 12. The jaw 11 is fixedly attached to or integrated with the arm 3. The jaw 12 is rotatably arranged on a rivet 13 at the end of the arm 3 and is connected to the pull rod 6 by means of a rivet 14. The tool 4 thus is arranged, in the normal position when the pull rod 6 is in the extended position, to have the jaws 11 and 12 separated, and, when the pull rod 6 during operation is in a retracted position, to have the jaws 11 and 12 closed. This embodiment involving a stationary jaw 11 and a movable jaw 12 has the advantage of having a so-called "immovable" or steady tip, in contrast to a device with two movable parts, such as a pair of scissors with two blades. This is especially important when operating under microscope, where one wants to be able to operate the tool without it disappearing from the lens coverage of the microscope.

In this embodiment, the tubular arm 3 is made of a memory metal, preferably a nickel titanium alloy under the trademark "NITINOL SE 508" supplied by Nitinol Devices & Components, Fremont, Calif. Data of the material are shown in Table 1.

TABLE 1

| | |
|---|---|
| Nickel (atomic percentage) | 50.8 ± 0.3 |
| Titanium (atomic percentage) | balance |
| Oxygen (vppm) | max. 500 |

The material has a transformation temperature of min. 45° C. The arm 3 has an outer diameter of 2.2±0.05 mm and an inner diameter of 1.27±0.05 mm. The wall thickness of the arm 3 is 0.465 mm. Moreover, the arm 3 is in the embodiment illustrated about 180 mm long.

The pull rod 6 is made of stainless steel and has a diameter of 0.7 mm.

When using the device, the arm 3 is bent to the shape which is suitable for the application. After being used, the device 1 is placed in an autoclave for sterilisation. In the autoclave treatment, the device 1 is heated above its transformation temperature and resumes its original shape. Of course, it is possible to thermally treat the device 1 in a number of different ways to make it resume its original shape.

The arm 3 and the tool 4 are preferably arranged to be exchangeable at the handle 2.

Also other alloys and materials than the one stated above can be used. For instance, there are certain copper alloys, iron-base materials and even polymeric materials that have "memory" properties. Up to now, nickel-titanium alloys are preferred for clinical use. However, it is important for the material to be compatible with the human body in the application involved and not to have a transformation temperature which is so low that the device 1 is affected to a considerable extent by the heat of the human body or by thermal radiation from surgical lighting and the like.

The invention is not limited to that described above or shown in the drawing and can be modified within the scope of the appended claims.

What is claimed is:

1. A surgical device (1) comprising:
    an elongate, flexible and tubular arm (3) which has a distal end and a proximal end;
    a flexible pulling means (6) which is movably arranged inside the arm (3) essentially over the entire length thereof;
    a tool (4) which is arranged at the distal end of the arm (3) and which comprises at least two parts (11, 12), which are arranged movable in relation to each other by operation of said pulling means (6); and
    an operating means (15) which is arranged at the proximal end of the arm to operate said pulling means (6) and, thus, said tool (4), characterised in that said arm (3) is made of a material which resumes its shape by heating, preferably a memory metal, which has a transformation temperature which allows the arm (3) to be deformable to the desired shape at room temperature and to keep the thus obtained shape at a patient's body temperature during use of the device (1), so as then to allow resumption of its original shape when exposed to a temperature exceeding the body temperature.

2. A surgical device (1) as claimed in claim 1, characterised in that said material is a nickel-titanium alloy.

3. A surgical device (1) as claimed in claim 2, characterised in that said pulling means (6) is made of a material other than that of the arm (3).

4. A surgical device (1) as claimed in claim 2, characterised in that said arm (3) is arranged rotatable in relation to the handle (2).

5. A surgical device (1) as claimed in claim 2, characterised in that said arm (3) and said tool (4) are arranged to be exchangeable.

6. A surgical device (1) as claimed in claim 2, characterised in that said material comprises nickel in the range 50 to 52 atomic percentage and titanium in the range 48 to 50 atomic percentage.

7. A surgical device (1) as claimed in claim 6, characterised in that said pulling means (6) is made of a material other than that of the arm (3).

8. A surgical device (1) as claimed in claim 6, characterised in that said arm (3) is arranged rotatable in relation to the handle (2).

9. A surgical device (1) as claimed in claim 6, characterised in that said arm (3) and said tool (4) are arranged to be exchangeable.

10. A surgical device (1) as claimed in claim 6, characterised in that said material comprises nickel in the range 50.6 to 51 atomic percentage and titanium in the range 49 to 49.4 atomic percentage.

11. A surgical device (1) as claimed in claim 10, characterised in that said pulling means (6) is made of a material other than that of the arm (3).

12. A surgical device (1) as claimed in claim 10, characterised in that said arm (3) is arranged rotatable in relation to the handle (2).

13. A surgical device (1) as claimed in claim 10, characterised in that said arm (3) and said tool (4) are arranged to be exchangeable.

14. A surgical device (1) as claimed in claim 1, characterised in that said pulling means (6) is made of a material other than that of the arm (3).

15. A surgical device (1) as claimed in claim 14, characterised in that said arm (3) is arranged rotatable in relation to the handle (2).

16. A surgical device (1) as claimed in claim 14, characterised in that said pulling means (6) comprises a wire whose one end is attached to a movable part (12) of the tool (4) which cooperates with a stationary part (11) of the tool (4), and whose other end is fixed to a connection component with stop elements (7, 8); and
    said at least one wire is made of stainless steel.

17. A surgical device (1) as claimed in claim 16, characterised in that said operating means (15) comprises a first lever (16) which is connected to a second lever (17) and which is angled in relation to said second lever (17), the operating means (15) being tiltably fixed to a handle (2) by means of a fixing element (18) in such a manner that, when the first lever (16) is pressed towards the handle (2), the second lever (17) is made to tilt away from the handle (2) and vice versa, and the second lever (17) being provided to engage between the stop elements (7, 8) to operate said pulling means (6).

18. A surgical device (1) as claimed in claim 17, characterised by a pressure spring (19) which is arranged in a biasing manner between the handle (2) and the first lever (16), the first lever (16) being, in the normal position, pressed away from the handle (2) and the second lever (17) being pressed towards the handle (2).

19. A surgical device (1) as claimed in claim 1, characterised in that said arm (3) is arranged rotatable in relation to the handle (2).

20. A surgical device (1) as claimed in claim 1, characterised in that said arm (3) and said tool (4) are arranged to be exchangeable.

* * * * *